US009700617B2

(12) United States Patent
Berggren (10) Patent No.: US 9,700,617 B2
(45) Date of Patent: Jul. 11, 2017

(54) METHODS FOR TREATING AND/OR LIMITING DEVELOPMENT OF DIABETES IN SUBJECTS WITH AMYOTROPHIC LATERAL SCLEROSIS (71) Applicant: Biocrine AB, Solna (SE)

(72) Inventor: Per Olof Berggren, Solna (SE)

(73) Assignee: BioCrine AB, Solna (SE)

( * ) Notice: Subject to any disclaimer, the term of this patent is extended or adjusted under 35 U.S.C. 154(b) by 0 days.

(21) Appl. No.: 15/017,989

(22) Filed: Feb. 8, 2016

(65) Prior Publication Data
US 2016/0228545 A1 Aug. 11, 2016

Related U.S. Application Data (60) Provisional application No. 62/113,669, filed on Feb. 9, 2015.

(51) Int. Cl.
*A61K 39/00* (2006.01)
*A61K 39/395* (2006.01)
*A61K 31/713* (2006.01)
*A61K 31/7088* (2006.01)
*A61K 31/455* (2006.01)
*A61K 31/554* (2006.01)
*A61K 31/277* (2006.01)
*A61K 31/4422* (2006.01)
*A61K 31/7105* (2006.01)
*A61K 45/06* (2006.01)
*G01N 33/68* (2006.01)

(52) U.S. Cl.
CPC ........ *A61K 39/3955* (2013.01); *A61K 31/277* (2013.01); *A61K 31/4422* (2013.01); *A61K 31/455* (2013.01); *A61K 31/554* (2013.01); *A61K 31/7088* (2013.01); *A61K 31/713* (2013.01); *A61K 31/7105* (2013.01); *A61K 39/395* (2013.01); *A61K 45/06* (2013.01); *G01N 33/6854* (2013.01); *G01N 2800/042* (2013.01); *G01N 2800/28* (2013.01); *G01N 2800/50* (2013.01)

(58) Field of Classification Search
None
See application file for complete search history.

(56) References Cited

FOREIGN PATENT DOCUMENTS

WO 2010/060100 A2 5/2010

OTHER PUBLICATIONS http://www.webmd.com/diabetes/tc/diabetes-differences-between-type-1-and-2-topic-overview, downloaded Apr. 5, 2017.*
Edri-Brami et al. 2012. PLoS One. 7:e35772.*
Engelhardt et al. Synapse 1995. 20:185-199.*
Mosier et al. 1995. Ann. Neurol. 37:102-109.*
Smith et al. 1992. NEJM. 327:1721-8.*
Appel SH, Zhao W, Beers DR, Henkel JS. The microglial-motoneuron dialogue in ALS. Acta Myol. 2011;30(1):4-8.
Barber SC, Shaw PJ. Oxidative stress in ALS: key role in motor neuron injury and therapeutic target. Free Radic Biol Med. 2010;48(5):629-641.
Berggren PO, et al. Removal of Ca2+ channel B3subunit enhances Ca2+ oscillation frequency and insulin exocytosis. Cell. 2004;119(2):273-284.
Brooks BR. Natural history of ALS: symptoms, strength, pulmonary function, and disability. Neurology. 1996;47(4 Suppl 2):S71-81.
Billups B, Forsythe ID. Presynaptic mitochondrial calcium sequestration influences transmission at mammalian central synapses. J Neurosci. 2002;22(14):5840-5847.
Craft S, Watson GS. Insulin and neurodegenerative disease: shared and specific mechanisms. Lancet Neural. 2004;3(3):169-178.
Dupuis L, Oudart H, Rene F, Gonzalez de Aguilar JL, Loeffler JP. Evidence for defective energy homeostasis in amyotrophic lateral sclerosis: benefit of a high-energy diet in a transgenic mouse model. Proc Natl Acad Sci USA. 2004;101(30)11159-11164.
Fratantoni SA, Weisz G, Pardal AM, Reisin RC, Uchitel OD. Amyotrophic lateral sclerosis IgG-treated neuromuscular junctions develop sensitivity to L-type calcium channel blacker. Muscle Nerve. 2000;23(4):543-550.
Fridlyand Le, Tamarina N, Philipson LH. Bursting and calcium oscillations in pancreatic beta-cells: specific pacemakers for specific mechanisms. Am J Physiol Endocrinol Metab. 2010;299(4):E517-532.
Gonzalez LE, et al. Amyotrophic lateral sclerosis-immunoglobulins selectively interact with neuromuscular junctions expressing P/Q-type calcium channels. J Neurochem. 2011;119(4):826-838.
Halter, et al., "Oxidative stress in skeletal muscle stimulates early expression of Rad in a mouse model of amyotrophic lateral sclerosis," Free Radical Biology and Medicine, 48(7): 915-923, Apr. 2010.
Jawaid A, et al. ALS disease onset may occur later in patients with pre-morbid diabetes mellitus. Eur J Neurol. 2010;17(5):733-739.
Kimura F, et al. Amyotrophic lateral sclerosis patient antibodies label Ca2+ channel alpha 1 subunit. Ann Neurol. 1994;35(2)164-171.
Llinas R, et al. IgG from amyotrophic lateral sclerosis patients increases current through P-type calcium channels in mammalian cerebellar Purkinje cells and in isolated channel protein in lipid bilayer. Proc Natl Acad Sci USA. 1993;90(24):11743-11747.
Losavio A, Muchnik S. Spontaneous acetylcholine release in mammalian neuromuscular junctions. The American journal of physiology. 1997;273(6 Pt 1):C1835-1841.

(Continued)

*Primary Examiner* — Shulamith H Shafer
(74) *Attorney, Agent, or Firm* — McDonnell Boehnen Hulbert & Berghoff LLP (57) ABSTRACT Methods for treating and/or limiting development of diabetes in a subject with amyotrophic lateral sclerosis (ALS) by inhibiting IgG-mediated activation of voltage-gated calcium channels (VGCCs) in cells of the subject, by one or more of removing IgG from blood of the subject, blocking IgG from activating VGCCs in the subject; or blocking VGCCs in the subject are described, as are methods for identifying ALS patients at risk of developing diabetes.

12 Claims, 7 Drawing Sheets

(56) References Cited

OTHER PUBLICATIONS

Milosevic M, et al. Immunoglobulins G from patients with sporadic amyotrophic lateral sclerosis affects cytosolic Ca2+ homeostasis in cultured rat astrocytes. Cell Calcium. 2013;54(1):17-25.

Mosier DR, et al. Amyotrophic lateral sclerosis immunoglobulins increase Ca2+ currents in a motoneuron cell line. Ann Neurol. 1995;37(1):102-109.

Muchnik S, Losavio A, De Lorenzo S. Effect of amyotrophic lateral sclerosis serum on calcium channels related to spontaneous acetylcholine release. Clin Neurophysiol. 2002;113(7):1066-1071.

Park SA. A common pathogenic mechanism linking type-2 diabetes and Alzheimer's disease: evidence from animal models. J Clin Neurol. 2011;7(1):10-18.

Pradat PF, et al. Impaired glucose tolerance in patients with amyotrophic lateral sclerosis. Amyotroph Lateral Scler. 2010;11(1-2)166-171.

Pullen AH, Demestre M, Howard RS, Orrell RW. Passive transfer of purified IgG from patients with amyotrophic lateral sclerosis to mice results in degeneration of motor neurons accompanied by Ca2+ enhancement. Acta Neuropathol. 2004;107(1):35-46.

Renton AE, Chio A, Traynor BJ. State of play in amyotrophic lateral sclerosis genetics. Nat Neurosci. 2014;17(1):17-23.

Robberecht W, Philips T. The changing scene of amyotrophic lateral sclerosis. Nat Rev Neurosci. 2013;14(4)248-264.

Rorsman P, Braun M, Zhang Q. Regulation of calcium in pancreatic A- and B-cells in health and disease. Cell Calcium. 2012;51(3-4):300-308.

Rosen DR, et al. Mutations in Cu/Zn superoxide dismutase gene are associated with familial amyotrophic lateral sclerosis. Nature. 1993;362(6415):59-62.

Shi P, Gal J, Kwinter DM, Liu X, Zhu H. Mitochondrial dysfunction in amyotrophic lateral sclerosis. Biochim Biophys Acta. 2010;1802(1):45-51.

Smith RG, Alexianu ME, Crawford G, Nyormoi O, Stefani E, Appel SH. Cytotoxicity of immunoglobulins from amyotrophic lateral sclerosis patients on a hybrid motoneuron cell line. Proc Natl Acad Sci USA. 1994;91(8)3393-3397.

Smith RG, et al. Serum antibodies to L-type calcium channels in patients with amyotrophic lateral sclerosis. N Engl J Med. 1992;327(24):1721-1728.

Sun, et al. "Therapeutic potential of N-acetyl-glucagon-like peptide-1 in primary motor neuron cultures derived from non-transgenic and S0D1-G93A ALS mice," Cellular and Molecular Neurobiology, 33(3): 347-357, Dec. 2012.

Tran LT, Gentil BJ, Sullivan KE, Durham HD. The voltage-gated calcium channel blocker lomerizine is neuroprotective in motor neurons expressing mutant SOD1, but not TDP-43. J Neurochem. 2014;130(3):455-466.

Yang SN, Shi Y, Yang G, Li Y, Yu J, Berggren PO. Ionic mechanisms in pancreatic beta cell signaling. Cell Mol Life Sci. 2014;71(21):4149-4177.

Yang SN, Berggren PO. The role of voltage-gated calcium channels in pancreatic B-cell physiology and pathophysiology. Endocr. Rev. 2006;27(6):621-676.

International Search Report PCT/EP2016/052638, mailed Apr. 28, 2016.

\* cited by examiner

Figure 7

METHODS FOR TREATING AND/OR LIMITING DEVELOPMENT OF DIABETES IN SUBJECTS WITH AMYOTROPHIC LATERAL SCLEROSIS

CROSS-REFERENCE

This application claims priority to U.S. Provisional Patent Application Ser. No. 62/113,669 filed Feb. 9, 2015, incorporated by reference herein in its entirety.

INTRODUCTION

A defective metabolic energy homeostasis, i.e. glucose intolerance and insulin resistance, has been observed in both amyotrophic lateral sclerosis (ALS) patients and a transgenic mouse model. Approximately two-thirds of ALS patients develop a metabolic disorder like diabetes. Thus, methods for treating and limiting development of diabetes in ALS patients are needed.

SUMMARY OF THE INVENTION

In one aspect, the invention provides methods for treating and/or for limiting development of diabetes in a subject with amyotrophic lateral sclerosis (ALS), comprising inhibiting IgG-mediated activation of voltage-gated calcium channels (VGCCs) in cells of the subject, wherein the inhibiting comprises one or more of:
  (i) removing IgG from blood of the subject;
  (ii) blocking IgG from activating VGCCs in the subject; and
  (iii) blocking VGCCs in the subject.

In one embodiment, the inhibiting comprises removing serum IgG from the subject for a time sufficient to treat or limit development of diabetes in the subject, wherein the removing comprises contacting blood obtained from the subject with an IgG adsorbent, for a time and under conditions suitable to promote IgG adsorption onto the adsorbent. In a further embodiment, the IgG adsorbent includes, but is not limited to, anti-human IgG antibodies. In another embodiment, the inhibiting comprises blocking IgG from activating VGCCs, wherein the blocking comprises administering to the subject an amount effective of an inhibitor of IgG expression or activity to treat or limit development of diabetes in the subject, wherein the inhibitor may include but is not limited to anti-IgG antibodies, IgG blocking aptamers, IgG small interfering RNAs, IgG small internally segmented interfering RNAs, IgG short hairpin RNAs, IgG microRNAs, and IgG antisense oligonucleotides. In a still further embodiment, the inhibiting comprises blocking VGCCs in the subject, wherein the blocking comprises administering to the subject an amount effective of an inhibitor of VGCC expression or activity to treat or limit development of diabetes in the subject, wherein the inhibitor may include but is not limited to $Ca^{2+}$ channel blockers, VGCC-specific antibodies, aptamers, small interfering RNAs, small internally segmented interfering RNAs, short hairpin RNAs, microRNAs, and/or antisense oligonucleotides. For example, the inhibitor may be an inhibitor of VGCCs, including but not limited to phenylalkylamines, benzothiazepines, and dihydropyridines. In other embodiments, the inhibitor of VGCCs may include, but is not limited to nisoldipine (Sular), nifedipine (Adalat, Procardia), nicardipine (Cardene), isradipine (Dynacirc), nimodipine (Nimotop), felodipine (Plendil), amlodipine (Norvasc), diltiazem (Cardizem), lacidipine, lercanidipine, and verapamil (Calan, Isoptin). In one embodiment, the method treats or limits development of type 2 diabetes. In another embodiment, the method limits development of type 1 diabetes.

In another aspect, the invention provides methods for identifying an ALS patient at risk of developing diabetes, comprising
  a) contacting cells with a blood sample from a subject with ALS;
  b) measuring an $[Ca^{2+}]_i$ oscillation pattern and/or whole cell $Ca^{2+}$ current and comparing the measured oscillation pattern and/or whole cell $Ca^{2+}$ current to control; and
  c) identifying those subjects with an altered $[Ca^{2+}]_i$ oscillation pattern and/or whole cell $Ca^{2+}$ current relative to control as at risk for developing diabetes.

In another aspect, the invention provides methods for identifying an ALS patient at risk of developing diabetes, comprising:
  a) determining a level of IgG in a blood sample obtained from a subject with ALS;
  b) comparing the level of IgG in the blood sample to control; and
  c) identifying those subjects with an elevated level of IgG in the blood sample as at risk for developing diabetes.

In a still further aspect, the invention provides methods for identifying candidate compounds to treat and/or limit development of diabetes in a subject with ALS, comprising
  a) contacting a first population of cells and a second population of cells with a blood sample from a subject with ALS and diabetes, and further contacting the second population of pancreatic cells with one or more test compounds;
  b) measuring an $[Ca^{2+}]_i$ oscillation pattern and/or whole cell $Ca^{2+}$ current in the first population and the second population; and
  c) identifying those compounds that result in a reduced alteration of the $[Ca^{2+}]_i$ oscillation pattern and/or whole cell $Ca^{2+}$ current in the second population relative to the first population as candidate compounds for treating and/or limiting development of diabetes in a subject with ALS.

In one embodiment of any of these aspects, the cells, or the first population of cells and the second population of cells comprise pancreatic islet cells, muscle cells, vascular smooth muscle cells, cardiomyocytes, and/or nerve cells. In a further embodiment, the cells, or the first population of cells and the second population of cells comprise pancreatic cells, and wherein the pancreatic cells comprise pancreatic islets, pancreatic β-cells, and/or pancreatic α-cells. In another embodiment, the contacting is done in the presence of stimulatory glucose concentrations, stimulatory potassium concentrations, and/or wherein a depolarizing voltage is applied to the first population of cells and the second population of cells. In further embodiments, the blood sample may be whole blood, serum, or blood plasma.

DESCRIPTION OF THE FIGURES

FIG. 1. Disturbed glucose homeostasis in ALS-Tg mice and ALS serum-induced deterioration in pancreatic islet cell function. (A) Intraperitoneal glucose tolerance tests in 7-8 weeks old ALS-Tg (TG) and wild type (WT) mice. (B) Insulin secretion from islets isolated from wild-type and ALS-Tg mice and exposed to 3.3 and 11.1 mM glucose (Glu). (C) Glucose-induced $[Ca^{2+}]_i$ oscillation patterns in islets from WT and ALS-Tg mice. Representative $[Ca^{2-}]_i$ traces out of a total of 95 in wild-type group (upper) and 98 in ALS-Tg group (lower). (D) Delta fura-2 340/380 ratios showing K$^+$ depolarization-induced net increases in [Ca$^{2+}$]$_i$ in WT and ALS-Tg islets. (E) Morphological changes in islets incubated with normal fetal bovine serum (FBS, upper), control serum (CTL, middle) from patients with diabetes but no ALS and human ALS serum (ALS, lower) for 10 hours. (F) Representative [Ca$^{2+}$]$_i$ traces out of a total of 33, 72 and 40 recordings in FBS, CTL and ALS groups, respectively, obtained from islets isolated from 5 mice. (G) Insulin secretion from islets treated with ALS serum (n=3) and CTL serum (n=2), where n indicates the number of ALS- and CTL patients, for 10 hours and then challenged with 3.3 and 11.1 mM glucose for 30 minutes. (H) Summary of net insulin secretion from islets subjected to incubation with ALS or CTL patient sera. Data are presented as mean±SEM, *P<0.05.

FIG. 3. IgG purified from human ALS serum interferes with islet cell function and survival. (A) Averaged [Ca$^{2+}$]$_i$ responses to K$^+$ depolarization in mouse islet cells exposed overnight to either CTL IgG or ALS IgG. (B) Delta fura-2 340/380 ratios showing mean net increases in [Ca$^{2+}$]$_i$ in cells treated with control IgG, ALS IgG or boiled ALS IgG (n=2, 3, 3), where n indicates the number of CTL and ALS patients. (C) Averaged WST-1 absorbance showing the viability of islet cells following 24-h exposure to IgGs purified from two CTL subjects and three ALS patients as well as FBS. (D) Averaged WST-1 absorbance showing the viability of islet cells treated for 24 hours with patients' IgGs with and without boiling (n=3). (E) Averaged changes in [Ca$^{2+}$]$_i$ responses to K$^+$ depolarization in αTC1-6 cells following overnight incubation with either CTL-IgG or ALS-IgG. (F) Delta fura-2 340/380 ratios showing averaged net increases in [Ca$^{2+}$]$_i$ in αTC1-6 cells subjected to overnight treatment with CTL IgG, ALS IgG or boiled ALS-IgG (n=2, 3, 2). (G) Averaged WST-1 absorbance showing the viability of αTC1-6 cells exposed for 24 hours to purified CTL IgG, ALS IgG and boiled ALS IgG (n=2, 3, 2; where n indicates the number of CTL and ALS patients). Data are presented as mean±SEM. *P<0.0005, P<0.005 and *P<0.05.

FIG. 7. CTL-IgG and ALS-IgG time-Dependently Induced αTC1-6 Cell Death. (A) Summary graph showing averaged WST-1 absorbance, reflecting metabolically active viable cells, in cells exposed to control IgG or human ALS IgG for 12, 24 and 48 h, respectively. In normal FBS containing media, αTC1-6 cell number increased with incubation time. On the contrary, the number of αTC1-6 cells decreased with incubation time in the presence of IgG. When αTC1-6 cells were incubated with 100 µg IgG, there was no difference in viability between CTL-IgG and ALS-IgG occurring after 12 hours. For the cell viability test, we therefore used 100 µg of IgG and an incubation period of 24 hours (n=2). (B, C) [Ca$^{2+}$]$_i$ response to K$^+$ depolarization in αTC1-6 cells in the absence and presence of extracellular Ca$^{2+}$. A total of 127 [Ca$^{2+}$]$_i$ traces are shown in B and C.

DETAILED DESCRIPTION OF THE INVENTION

Within this application, unless otherwise stated, the techniques utilized may be found in any of several well-known references such as: *Molecular Cloning: A Laboratory Manual* (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the invention provides methods for treating and/or for limiting development of diabetes in a subject with ALS, comprising inhibiting IgG-mediated activation of voltage-gated calcium channels (VGCCs) in cells of the subject, wherein the inhibiting comprises one or more of:

(i) removing IgG from blood of the subject;
(ii) blocking IgG from activating VGCCs in the subject; and
(iii) blocking VGCCs in the subject.

As shown in the examples that follow, the inventor has discovered that ALS impairs glucose homeostasis partly due to decreased insulin release as a consequence of beta-cell failure, which is induced by defective cytosolic free $Ca^{2+}$ concentration ($[Ca^{2+}]_i$) handling driven by an ALS-IgG-induced hyper-activation of VGCCs. Thus, methods that limit the ability of IgG to activate VGCCs in an ALS subject can be used to treat or limit development of diabetes in the ALS subject.

The methods of the invention are carried out on a subject that has ALS. Any subject that is susceptible to ALS can be treated with the methods of the invention, including but not limited humans.

In one embodiment, the method is for treating diabetes. In this embodiment, the ALS subject has been diagnosed with type 1 or type 2 diabetes. As used herein, "diabetes" is characterized by insufficient or no production of insulin by the pancreas, leading to high blood sugar levels. As used herein, "treating diabetes" means accomplishing one or more of the following: (a) reducing the severity of the diabetes or diabetic complications; (b) limiting or preventing development of diabetic complications; (c) inhibiting worsening of diabetic complications or of symptoms characteristic of diabetes; (d) limiting or preventing recurrence of diabetic complications or of symptoms characteristic of diabetes; (e) limiting or preventing recurrence of diabetic complications or of symptoms characteristic of diabetes in subjects that were previously symptomatic.

Symptoms characteristic of diabetes include, but are not limited to, elevated blood glucose levels, decreased insulin production, insulin resistance, increased urinary frequency (polyuria), thirst (polydipsia), hunger (polyphagia) and unexplained weight loss. Diabetic complications that can be treated according to the methods of the invention include, but are not limited to, complications in the nerves (such as diabetic neuropathy), proteinuria, and impaired glomerular clearance, and complications associated with smooth muscle cell dysregulaton (including but not limited to erectile dysfunction, bladder dysfunction, and vascular complications including but not limited to atherosclerosis, stroke, and peripheral vascular disease). Any amount of limiting of these symptoms/complications is of great benefit to an ALS subject with diabetes.

In another embodiment, the method is for limiting development of diabetes in the ALS subject. In this aspect, the ALS subject does not yet have diabetes. In one embodiment, the method limits development of type 2 diabetes in the subject; in another embodiment, the methods limit development of type 1 diabetes in the subject. In these embodiments, "limiting development of diabetes" may include, for example, limiting/slowing progression of hyperglycemia, insulin resistance, pancreatic beta cell death, reduced insulin production, and/or limiting/slowing progression of the subject to a clinical diagnosis of type 1 or type 2 diabetes. Any amount of limiting development of diabetes is of great benefit to an ALS subject.

As shown by the inventor herein, ALS impairs glucose homeostasis partly due to decreased insulin release as a consequence of beta-cell failure, which is induced by defective [Ca2+]i handling driven by an ALS-IgG-induced hyper-activation of VGCCs. The methods of the invention thus involve inhibiting IgG-mediated activation of VGCCs in cells of the subject. Any such inhibition can serve to treat and/or limit development of diabetes in the subject. In various embodiments such inhibition results in a 5%, 10%, 25%, 50%, or greater reduction in IgG-mediated activation of VGCCs in cells of the subject. Inhibiting IgG-mediated activation of VGCCs in various cell types in an ALS subject is of value; for example, such inhibition in pancreatic islet cells, blood vessel cells, muscle cells, nerve cells, etc. help to treat and/or limit development of diabetes in the subject.

In one embodiment, the inhibiting comprises removing serum IgG from the subject (i.e.: IgG depletion), wherein the inhibiting comprises removing serum IgG from the subject for a time sufficient to treat or limit development of diabetes in the subject, wherein the removing comprises contacting blood obtained from the subject with an IgG adsorbent, for a time and under conditions suitable to promote IgG adsorption onto the adsorbent. This embodiment is similar to dialysis, in which blood is removed from the subject, "cleaned", and returned to the subject with a reduced IgG content. The blood may comprise whole blood, or may be separated into plasma and cellular components. Any amount of reduction of IgG in the blood sample obtained from the subject is useful for treating and/or limiting development of diabetes in the subject. In various embodiments, the method results in adsorption of 5%, 10%, 25%, 50%, or more of the IgG in the subject's blood sample contacted with the IgG adsorbent. Any suitable IgG adsorbent can be used, including but not limited to anti-human IgG antibodies affixed to a solid support (i.e.: column immunoadsorption).

In one exemplary embodiment, IgG depletion comprises use of an immunoadsorption column containing anti-human IgG-conjugated to Sepharose™ beads. It is well within the level of those of skill in the art to determine appropriate conditions to carry out IgG depletion for a given subject in light of all factors for the subject, based on the teachings herein.

In another embodiment, the inhibiting comprises blocking IgG from activating VGCCs, wherein the blocking comprises administering to the subject an amount effective of an inhibitor of IgG expression or activity to treat or limit development of diabetes in the subject. As used herein, an "inhibitor" of expression and/or activity of IgG includes compounds that reduce the transcription of IgG DNA into mRNA, compounds that reduce translation of the IgG mRNA into protein, and compounds that reduce the ability of IgG to activate VGCCs. Such inhibiting can be complete inhibition or partial inhibition, such that the expression and/or activity of IgG is reduced, resulting in a reduced ability to activate VGCCs. In various non-limiting embodiments, the inhibitor may include but is not limited to anti-IgG antibodies, IgG blocking aptamers, IgG small interfering RNAs, IgG small internally segmented interfering RNAs, IgG short hairpin RNAs, IgG microRNAs, IgG antisense oligonucleotides, and any other inhibitor (such as a small molecule inhibitor) of IgG.

In another embodiment, the inhibiting comprises blocking VGCCs in the subject, wherein the blocking comprises administering to the subject an amount effective of an inhibitor of VGCC expression or activity to treat or limit development of diabetes in the subject. As used herein, an "inhibitor" of expression and/or activity of VGCC includes compounds that reduce the transcription of VGCC DNA into mRNA, compounds that reduce translation of the VGCC mRNA into protein, and compounds that reduce the activity of VGCCs. Such inhibiting can be complete inhibition or partial inhibition, such that the expression and/or activity of VGCCs are reduced. In various embodiments, the inhibitor may include but is not limited to $Ca^{2+}$ channel blockers, VGCC-specific antibodies, aptamers, small interfering RNAs, small internally segmented interfering RNAs, short hairpin RNAs, microRNAs, and/or antisense oligonucleotides.

In one embodiment, the inhibitor is an inhibitor of VGCCs, including but not limited to phenylalkylamines, benzothiazepines, and dihydropyridines. There are three classes of VGCC blockers, i.e., dihydropyridines, benzothiazepines and phenylalkylamines. Dihydropyridines have high selectivity of vascular L-type calcium channels, phenylalkylamines are relatively selective for cardiac L-type calcium channels, and benzothiazepines are intermediate and act on both cardiac and vascular L-type calcium channels. Exemplary VGCC blockers include, but are not limited to nisoldipine (SULAR®), nifedipine (ADALAT®, PROCARDIAL®), nicardipine (CARDENE®), isradipine (DYNACIRC®), nimodipine (NIMOTOP®), felodipine (PLENDIL®), amlodipine (NORVASC®), diltiazem (CARDIZEM®), lacidipine, lercanidipine, and verapamil (CALAN®, ISOPTIN®).

TABLE 1

|  | Class | Selectivity |
| --- | --- | --- |
| nisoldipine | Dihydropyridine | L-type |
| nifedipine | Dihydropyridine | L-type |
| Nicardipine | Dihydropyridine | L-type |
| Isradipine | Dihydropyridine | L-type |
| Nimodipine | Dihydropyridine | L-type |
| Felodipine | Dihydropyridine | L-type |
| Amlodipine | Dihydropyridine | L-type |
| Diltiazem | Benzothiazepine | L-type |
| Lacidipine | Dihydropyridine | L-type |
| Lercanidipine | Dihydropyridine | L-type |
| Verapamil | Phenylalkylamine | L-type |

In each of these embodiments, the therapeutic may be administered by any suitable route, including but not limited to oral, topical, parenteral, intranasal, pulmonary, or rectal in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. The therapeutic may be present in association with one or more non-toxic pharmaceutically acceptable carriers and/or diluents and/or adjuvants, and if desired other active ingredients. The therapeutic may be in a form suitable for oral use, for example, as tablets, troches, lozenges, aqueous or oily suspensions, dispersible powders or granules, emulsion, hard or soft capsules, or syrups or elixirs.

In another embodiment, the therapeutic can also be administered locally via implantation of a membrane, sponge, or other appropriate material onto which the composition of the invention has been absorbed or encapsulated. Where an implantation device is used, the device can be implanted into a desired location, such as into the pancreas, and delivery of the desired molecule can be via diffusion, timed-release bolus, or continuous administration.

The dosage range depends on the choice of the compound, the route of administration, the nature of the formulation, the subject's condition, and the judgment of the attending practitioner. For example, oral administration would be expected to require higher dosages than administration by intravenous injection. Variations in these dosage levels can be adjusted using standard empirical routines for optimization, as is well understood in the art Acceptable formulation materials preferably are nontoxic to recipients at the dosages and concentrations employed. The therapeutic can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same).

As shown in the examples that follow, the inventor has discovered that ALS impairs glucose homeostasis partly due to decreased insulin release as a consequence of beta-cell failure, which is induced by defective $[Ca^{2+}]_i$ handling driven by an ALS-IgG-induced hyper-activation of VGCCs. The resulting abnormalities include an altered $[Ca^{2+}]_i$ oscillation pattern and/or whole cell $Ca^{2+}$ current compared to control, which thus permits a method to identify those ALS subjects that are at risk of developing diabetes, and thus can be treated according to the methods of the invention (i.e.: to limit development of diabetes).

Thus, in another aspect, the invention provides methods for identifying an ALS subject at risk of developing diabetes, comprising
a) contacting cells with a blood sample from a subject with ALS;
b) measuring an $[Ca^{2+}]_i$ oscillation pattern and/or whole cell $Ca^{2+}$ current and comparing the measured oscillation pattern and/or whole cell $Ca^{2+}$ current to control; and
c) identifying those subjects with an altered $[Ca^{2+}]_i$ oscillation pattern and/or whole cell $Ca^{2+}$ current relative to control as at risk for developing diabetes.

The blood sample can be whole blood, serum, blood plasma, or any other suitable blood sample in which circulating IgG from an ALS subject may be present. For example, the blood sample may be a plasma sample. As used herein, a "plasma sample" means blood plasma, the liquid component of blood, and is prepared, for example, by centrifugation of whole blood to remove blood cells. As used herein, a plasma sample also includes a blood serum sample, in which blood clotting factors have been removed.

Any suitable cells can be used in the methods of the invention, including but not limited to pancreatic islet cells, muscle cells, vascular smooth muscle cells, cardiomyocytes, nerve cells, etc. In one embodiment, the cells comprise pancreatic islets. The contacting of the cells with the blood sample can be in vitro or in vivo (ex: in an experimental animal model); in one embodiment the contacting occurs in vitro. Any suitable conditions can be used for carrying out the methods of the invention. In one embodiment, the cells are contacted with the blood sample under stimulatory glucose concentrations. Such stimulatory glucose concentrations may be between 6 mM-20 mM glucose; alternatively between 6 mM-15 mM glucose; between 10-12 mM glucose, or about 11 mM glucose. In another embodiment, the contacting is done under conditions suitable to open the calcium channels in the cells. For example, a depolarizing voltage (−50 to 50 mV) can be applied to the cells. Alternatively (or in combination), the cells are contacted with the blood sample under potassium concentrations sufficient to open calcium channels in the cells. Such stimulatory potassium concentrations may be between 25 mM and 50 mM potassium; alternatively between 25 mM-40 mM potassium; between 25-30 mM potassium, or about 25 mM potassium.

In a further embodiment, the cells are cultured at approximately 37° C. (preferably in a humidified incubator, such as 5% $CO_2$) prior to measuring an $[Ca^{2+}]_i$ oscillation pattern and/or whole cell $Ca^{2+}$ current at approximately room temperature. Techniques for measuring cellular $[Ca^{2+}]_i$ oscillation patterns and/or whole cell $Ca^{2+}$ current (such as by $[Ca^{2+}]_i$ single channel and whole-cell patch-clamp measurements (cell-attached and perforated whole-cell patch-clamp techniques) that are well known in the art), and other suitable assay conditions to carry out the methods of the invention are well within the level of those of skill in the art, based on the teachings herein.

Any suitable control can be used, including but not limited to a cell treated under the same conditions other than being contacted with the ALS subject's blood sample (for example, where the control cell is contacted with (i) a blood sample from a non-ALS subject, or (ii) contacted with an alternative control sample), or a predetermined $[Ca^{2+}]_i$ oscillation pattern and/or whole cell $Ca^{2+}$ current threshold, such that a $[Ca^{2+}]_i$ oscillation pattern and/or whole cell $Ca^{2+}$ current different (i.e.: more rapid oscillation pattern and/or higher whole cell $Ca^{2+}$ current threshold) from the threshold indicates a risk for developing diabetes. The difference from control that indicates a risk of developing diabetes in the ALS subject may be a difference of 10%, 25%, 50%, 100%, or more. In one embodiment, the difference is a statistically significant increase as judged by standard statistical analysis.

In one embodiment, the ALS subject is at risk of type 1 diabetes; in another embodiment, the ALS subject is at risk of type 2 diabetes.

In another aspect, the invention provides methods for identifying an ALS patient at risk of developing diabetes, comprising:
a) determining a level of IgG in a blood sample obtained from a subject with ALS;
b) comparing the level of IgG in the blood sample to control; and
c) identifying those subjects with an elevated level of IgG in the blood sample as at risk for developing diabetes.

The inventor has shown in the examples that follow that IgG-induces hyper-activation of VGCCs in ALS patients, leading to development of diabetes. Thus, ALS subjects at risk of developing diabetes can be identified by detecting an elevated level of IgG in the blood sample. The blood sample can be whole blood, serum, blood plasma, or any other suitable blood sample in which circulating IgG from an ALS subject may be present. For example, the blood sample may be a plasma sample.

Any suitable control can be used, including but not limited to a cell treated under the same conditions other than being contacted with the ALS subject's blood sample (for example, where the control cell is contacted with (i) a blood sample from a non-ALS subject, or (ii) contacted with an alternative control sample), or a predetermined IgG threshold, such that an IgG level above the threshold indicates a risk for developing diabetes. The difference from control that indicates a risk of developing diabetes in the ALS subject may be a difference of 10%, 25%, 50%, 100%, or more. In one embodiment, the difference is a statistically significant increase as judged by standard statistical analysis. Techniques for determining a level of IgG in the blood sample are well known to those of skill in the art.

In one embodiment, the ALS subject is at risk of type 1 diabetes; in another embodiment, the ALS subject is at risk of type 2 diabetes.

In another aspect, the invention provides methods for identifying candidate compounds to treat and/or limit development of diabetes in a subject with ALS, comprising
a) contacting a first population of cells and a second population of cells with a blood sample from a subject with ALS and diabetes, and further contacting the second population of pancreatic cells with one or more test compounds;
b) measuring an $[Ca^{2+}]_i$ oscillation pattern and/or whole cell $Ca^{2+}$ current in the first population and the second population; and
c) identifying those compounds that result in a reduced alteration of the $[Ca^{2+}]_i$ oscillation pattern and/or whole cell $Ca^{2+}$ current in the second population relative to the first population as candidate compounds for treating and/or limiting development of diabetes in a subject with ALS.

As shown in the examples that follow, the inventor has discovered that ALS impairs glucose homeostasis partly due to decreased insulin release as a consequence of beta-cell failure, which is induced by defective $[Ca^{2+}]_i$ handling driven by an ALS-IgG-induced hyper-activation of VGCCs.

The resulting abnormalities include an altered $[Ca^{2+}]_i$ oscillation pattern and/or whole cell $Ca^{2+}$ current compared to control, which thus permits a method to identify candidate compounds to treat and/or limit development of diabetes.

The blood sample can be whole blood, serum, blood plasma, or any other suitable blood sample in which circulating IgG from an ALS subject may be present. For example, the blood sample may be a plasma sample.

Any suitable cells can be used in the methods of the invention, including but not limited to pancreatic islet cells, muscle cells, vascular smooth muscle cells, cardiomyocytes, nerve cells, etc. In one embodiment, the cells comprise pancreatic islets. The contacting of the cells with the blood sample can be in vitro or in vivo (ex: in an experimental animal model); in one embodiment the contacting occurs in vitro. Any suitable conditions can be used for carrying out the methods of the invention. In one embodiment, the cells are contacted with the blood sample under stimulatory glucose concentrations. Such stimulatory glucose concentrations may be between 6 mM-20 mM glucose; alternatively between 6 mM-15 mM glucose; between 10-12 mM glucose, or about 11 mM glucose. In another embodiment, the contacting is done under conditions suitable to open the calcium channels in the cells. For example, a depolarizing voltage can be applied to the cells (−50 to 50 mV). Alternatively (or in combination), the cells are contacted with the blood sample under potassium concentrations sufficient to open calcium channels in the cells. Such stimulatory potassium concentrations may be between 25 mM and 50 mM potassium; alternatively between 25 mM-40 mM potassium; between 25-30 mM potassium, or about 25 mM potassium.

In a further embodiment, the cells are cultured at approximately 37° C. (preferably in a humidified incubator, such as 5% $CO_2$) prior to measuring an $[Ca^{2+}]_i$ oscillation pattern and/or whole cell $Ca^{2+}$ current at approximately room temperature. Techniques for measuring cellular $[Ca^{2+}]_i$ oscillation patterns and/or whole cell $Ca^{2+}$ current (such as by $[Ca^{2+}]_i$, single channel and whole-cell patch-clamp measurements (cell-attached and perforated whole-cell patch-clamp techniques) that are well known in the art), and other suitable assay conditions to carry out the methods of the invention are well within the level of those of skill in the art, based on the teachings herein.

The difference from control that indicates a test compound is a candidate compound for treating and/or limiting development of ALS may be a reduction of 10%, 25%, 50%, 100%, or more in cellular $[Ca^{2+}]_i$ oscillation patterns and/or whole cell $Ca^{2+}$ current. In one embodiment, the difference is a statistically significant increase as judged by standard statistical analysis. Techniques for measuring cellular $[Ca^{2+}]_i$ oscillation patterns and/or whole cell $Ca^{2+}$ current (such as by $[Ca^{2+}]_i$, single channel and whole-cell patch-clamp measurements (cell-attached and perforated whole-cell patch-clamp techniques that are well known in the art).

In one embodiment, the candidate compounds are candidate compounds for limiting development of and/or treating type 1 diabetes. In another embodiment, the candidate compounds are candidate compounds for limiting development of and/or treating type 2 diabetes. The present invention further provides compounds identified by the above screening methods, and their use for treating subjects in need thereof.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

EXAMPLES

Abstract

Patients with the neurodegenerative disease amyotrophic lateral sclerosis (ALS) often show hallmarks of type 2 diabetes mellitus (T2DM), such as impaired glucose homeostasis. Despite this important relation, the causal link between ALS and T2DM has remained a mystery. We now demonstrate that ALS is associated with impaired glucose homeostasis partly due to decreased insulin release resulting from altered beta-cell function and survival. The latter was induced by defect handling of cytosolic free $Ca^{2+}$ concentration ($[Ca^{2+}]_i$) driven by an ALS-IgG-induced hyper-activation of voltage-gated $Ca^{2+}$ channels. Similar effects of ALS-IgG on $[Ca^{2+}]_i$ and cell survival were established in αTC1-6 cells. Our findings thus indicate a mechanistic link between ALS and diabetes that may lay the foundation for a new pharmacological treatment strategy for patients suffering from a combination of these severe diseases.

Introduction

Amyotrophic lateral sclerosis (ALS) is a devastating neurodegenerative disease. Affected individuals show progressive dysfunction and degeneration of brainstem and spinal cord motor neurons. There is no clear therapeutic available for ALS and clinically ALS patients reveal advanced muscular weakness, paralysis and death within 2~5 years (1). The etiology of ALS is unknown but dysregulation of voltage-gated $Ca^{2+}$ channels (VGCCs) and thereby cytosolic free $Ca^{2+}$ concentration ($[Ca^{2+}]_i$) as well as synaptic plasticity have been proposed (2, 3). Also the immune system may contribute to the pathogenesis of ALS. Ultra-structural abnormalities with $Ca^{2+}$ accumulation in neuronal tissues and cells and increased transmitter release at motor neurons have been described in rodents treated with purified immunoglobulin G (IgG) from ALS patients (4). Increased $[Ca^{2+}]_i$ may lead to mitochondrial dysfunction, free radical damage and cellular cytotoxicity (5-7). A large number of neurodegenerative diseases, like ALS, are known to be associated with hallmarks of type 2 diabetes mellitus (T2DM), such as impaired glucose homeostasis, but the causal link is not known (8-10). The pancreatic islet has a central role in regulating blood glucose homeostasis. In the present study we tested the hypothesis that diabetes in association with ALS is caused by a circulating factor negatively affecting islet cell function and survival About 20% of patients with a familial history of ALS (fALS) have mutations in the $Cu^{2+}/Zn^{2+}$ superoxide dismutase (SOD1) gene (11). Recent studies have demonstrated that the chromosome 9 open reading frame (C9orf72) gene repeat expansion is the most common genetic cause of fALS in Western countries, and various genetic mutations including TDP43, FUS, OPTN, UBQLN2, and NEFH genes are also involved in responsible causes of fALS (12). Among various transgenic animal models of ALS, SOD1-mutated ($SOD1^{G93A}$) mice remain a reliable model for cell death mechanisms, especially focused on immune-inflammatory aspects that are similar to those revealed by pathological finding in ALS patients (13, 14).

Results and Discussion

Figure 1:
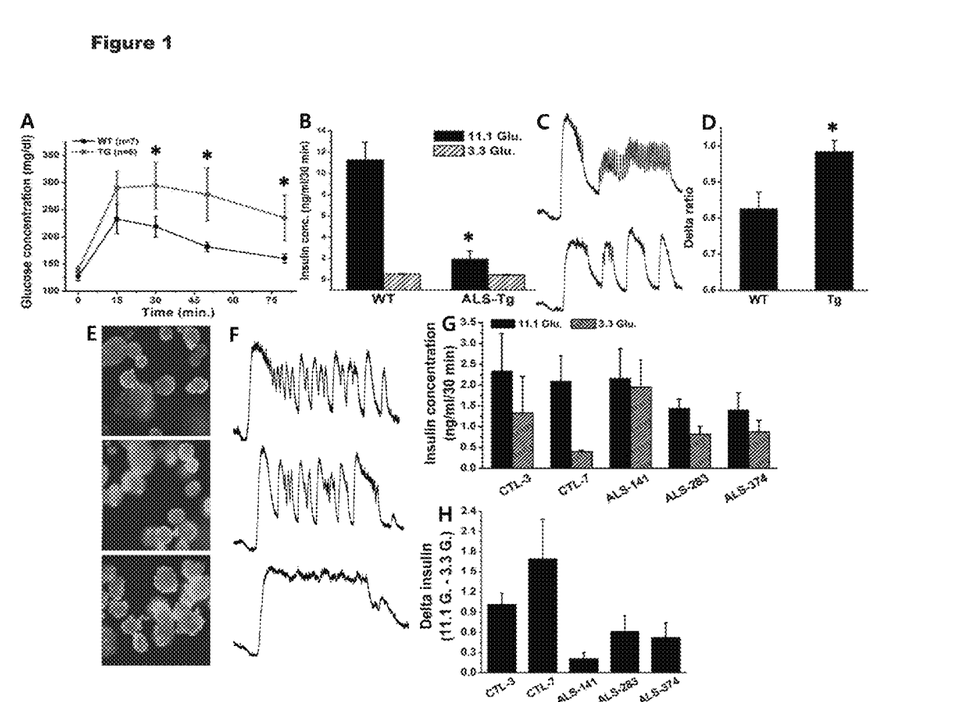
Figure 4:
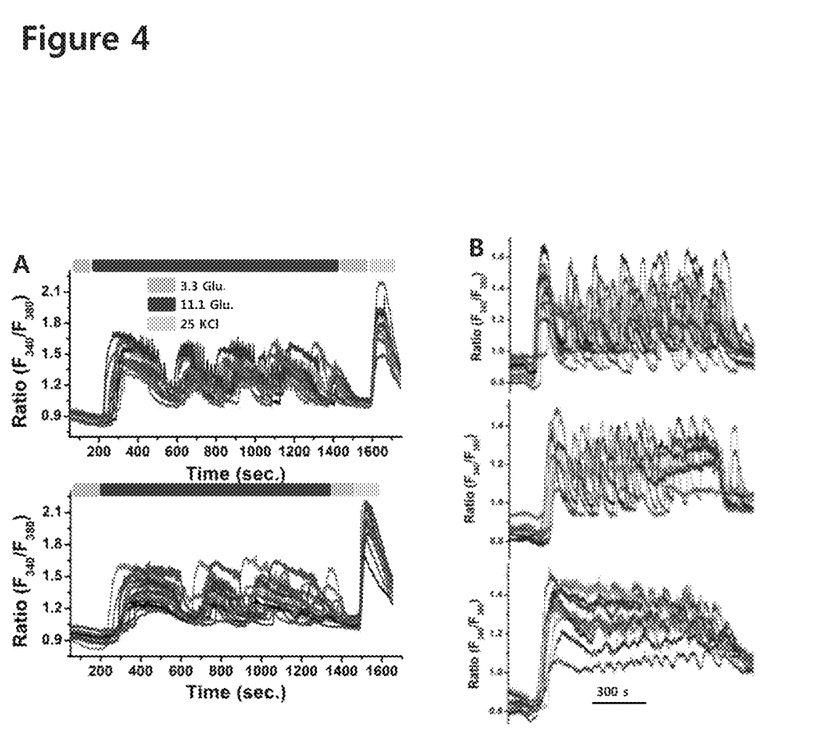
FIG. 4. Disturbed [Ca$^{2+}$]$_i$ handling in ALS-Tg mouse islets and ALS serum-treated mouse islets. (A) [Ca$^{2+}$]$_i$ traces registered before and during glucose (11.1 mM) and KCl (25 mM) stimulation in islets from wild-type (upper n=14) and ALS-Tg mice (lower, n=17). (B) [Ca$^{2+}$]$_i$ traces acquired before and during glucose (11.1 mM) in FBS-(upper, n=33), CTL serum-(middle, n=72) and ALS serum-treated wild-type mouse islets (lower, n=40).

We investigated various aspects of islet function using 7-8 weeks old $SOD1^{G93A}$ transgenic (ALS-Tg) mice and aged-matched controls. Intraperitoneal glucose tolerance tests were performed (FIG. 1A). ALS-Tg mice demonstrated a less efficient glucose homeostasis, shown by the less effective glucose clearance from the blood, compared to wild-type littermates. Islets from ALS-Tg mice showed considerably lower glucose-stimulated insulin release, compared to islets from wild-type mice (FIG. 1B). Glucose-stimulated insulin secretion results from increased beta-cell $Ca^{2+}$ influx through VGCCs and thereby an increase in $[Ca^{2+}]_i$. Glucose not only increases $[Ca^{2+}]_i$ but also causes $[Ca^{2+}]_i$ oscillation patterns in beta-cells as well as in islets with periods ranging from several seconds to several minutes (15-19). These types of $[Ca^{2+}]_i$ oscillation patterns are important for beta-cell function and survival and also serve as fingerprints for beta cell well-being. Next we therefore investigated changes in $[Ca^{2+}]_i$ subsequent to stimulation with high glucose. There was a noteworthy difference in the distribution of $[Ca^{2+}]_i$ oscillation patterns between islets from wild-type mice and islets from the ALS-Tg mice (FIG. 1C, D and FIG. 4A). In contrast to wild-type islets, islets from ALS-Tg mice showed a significant loss of the high-frequency type of $[Ca^{2+}]_i$ oscillations (FIG. 1C, D and Supplementary FIG. 1A). Also the $K^+$-induced increase in $[Ca^{2-}]_i$ was significantly different between ALS-Tg islets and control islets, the former being more pronounced (FIG. 1C, D and FIG. 4A).

To clarify whether there is a circulating factor in ALS patients with T2DM that may affect beta cell $[Ca^{2+}]_i$ handling, we investigated the effects of serum from ALS patients on $[Ca^{2+}]_i$ oscillations in mouse islets stimulated by 11 mM glucose. We were in the present study only using ALS serum from sporadic cases with T2DM. Compared with control serum or normal FBS containing media, islets exposed to ALS serum displayed a remarkable change in their $[Ca^{2+}]_i$ oscillation patterns which was paralleled by early morphological changes in islet shape (FIG. 1E, F and FIG. 4B). Representative $[Ca^{2+}]_i$ oscillation traces and means of combined $[Ca^{2+}]_i$ oscillation traces from different islets are shown for each experimental condition (FIG. 1F and FIG. 4B). We also investigated insulin secretion from intact islets exposed to ALS serum, control serum or FBS. There was no difference in glucose-induced insulin secretion from islets incubated in control serum or normal FBS, whereas islets incubated in ALS serum failed in terms of glucose response (FIG. 1G, H). These data are consistent with a circulating factor in serum from patients with ALS and T2DM that negatively impact on in vivo beta cell function and survival.

Figure 2:
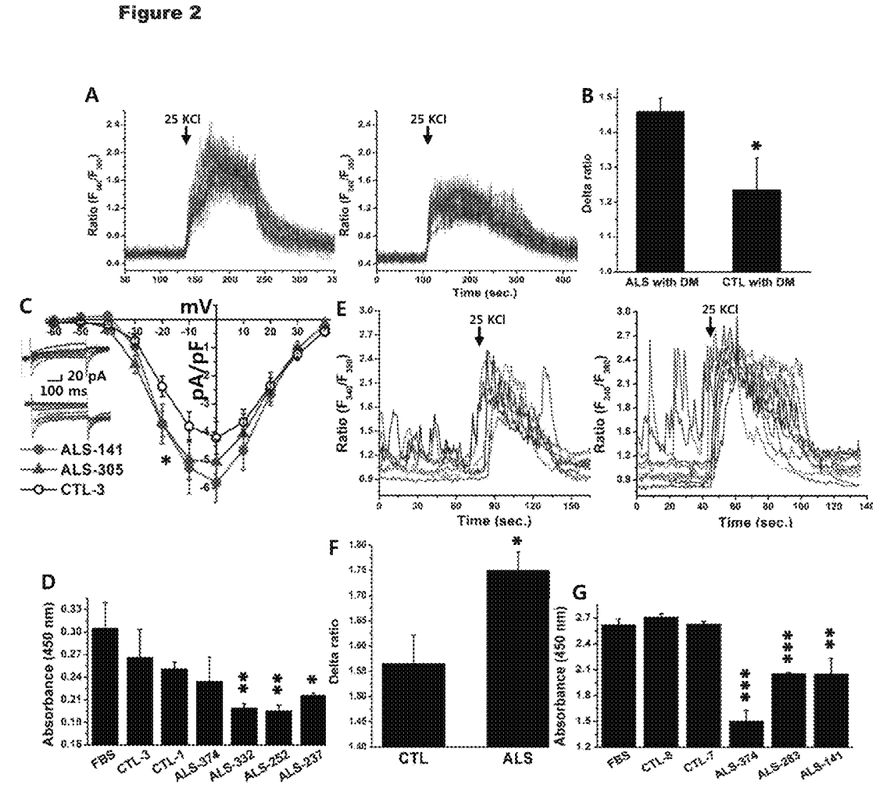
FIG. 2. Effects of ALS serum on [Ca$^{2+}$]$_i$ handling and viability in mouse pancreatic islet cells and glucagon-secreting αTC1-6 cells. (A) K$^+$ depolarization-induced [Ca$^{2+}$]$_i$ responses in mouse islet cells exposed to ALS serum (left) and CTL serum (right) obtained from patients with diabetes but no ALS. (B) Delta fura-2 340/380 ratios showing mean net increase in [Ca$^{2+}$]$_i$ induced by K$^+$ depolarization in mouse islet cells incubated with ALS serum and CTL serum. (C) Averaged current-voltage relationships of nifedipine-sensitive Ca$^{2+}$ channels in islet cells incubated with CTL serum and two ALS sera. Insets illustrating representative whole cell Ca$^{2+}$ currents in an ALS serum-treated cell (lower) and a cell incubated with control serum (upper). (D) Mean WST-1 absorbance showing the viability of dissociated islet cells exposed to ALS (n=4), CTL serum (n=2) or FBS. (E) Representative recordings of K$^+$ depolarization-induced [Ca$^{2+}$]$_i$ responses in control αTC1-6 cells (left) and αTC1-6 cells treated with ALS serum (right). (F) Delta fura-2 340/380 ratios showing mean net increases in [Ca$^{2+}$]$_i$ in cells treated with control serum-(n=2) and ALS serum-exposed αTC1-6 cells (n=4), where n indicates the number of CTL and ALS patients. (G) Averaged WST-1 absorbance showing the viability of αTC1-6 cells subsequent to exposure to ALS serum, CTL serum and FBS. Data are presented as mean±SEM. *P<0.0005, P<0.005 and *P<0.05.
Figure 5:
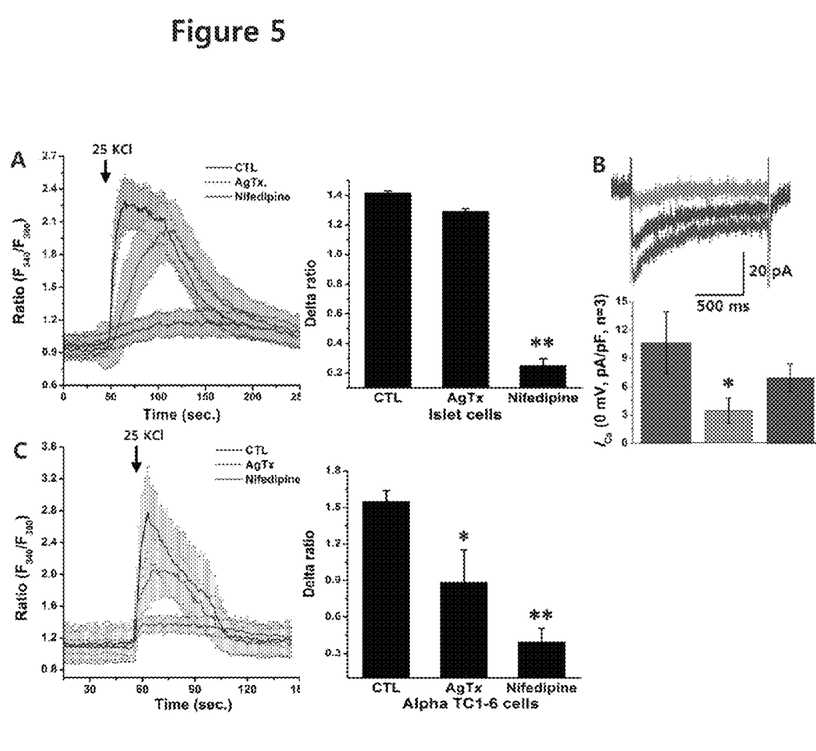
FIG. 5. Effects of the specific Ca$^{2+}$ channel blockers AgTx and nifedipine on K$^+$ depolarization-induced [Ca$^{2+}$]$_i$ responses and whole-cell Ca$^{2+}$ currents in mouse islet cells and αTC1-6 cells. (A) K$^-$ depolarization-induced [Ca$^{2+}$]$_i$ responses in control mouse islet cells and cells pre-treated with AgTx or nifedipine (left). Delta fura-2 340/380 ratios showing mean net increase in [Ca$^{2+}$]$_i$ induced by K$^+$ depolarization in control mouse islet cells and cells pre-treated with AgTx or nifedipine (right). (B) Representative whole-cell Ca$^{2+}$ currents in a mouse islet cell before (red) and during exposure to nifedipine (green) and after washing (blue) (upper). Average Ca$^{2+}$ current density in cells before (red) and during exposure to nifedipine (green) and after washing (blue) (n=3) (lower). (C) [Ca$^{2+}$]$_i$ responses to K$^+$ depolarization in control αTC1-6 cells and cells pre-exposed to AgTx or nifedipine (left). Delta fura-2 340/380 ratios showing mean net increase in [Ca$^{2+}$]$_i$ induced by K$^+$ depolarization in control αTC1-6 cells and cells pre-exposed to AgTx or nifedipine (right). Data are presented as mean±SEM, **P<0.005 and *P<0.05.

To gain further insight into the molecular mechanisms responsible for the observed changes in $[Ca^{2+}]_i$ handling in association with ALS, dissociated mouse pancreatic islet cells were incubated overnight with serum from T2DM patients with and without ALS. Sera from twelve ALS patients compared to sera from eight control patients induced a significantly higher transient increase in $[Ca^{2+}]_i$ when cells were depolarized with 25 mM KCl leading to an opening of VGCCs (FIG. 2A, B). The ALS serum-induced overload in $[Ca^{2+}]_i$ may lead to $Ca^{2+}$-dependent β cell destruction. Cell viability assay confirmed that there was a higher cytotoxicity in the islet cell population exposed to ALS patient serum than in those exposed to control serum or normal FBS overnight (FIG. 2D). To identify the VGCC participating in the transient increase in $[Ca^{2+}]_i$ we applied specific $Ca^{2+}$ channel blockers. FIGS. 5A and 5B shows that the L-type VGCC (nifedipine-sensitive) was the major channel responsible for the $[Ca^{2+}]_i$ increase in dissociated mouse islet cells. Representative traces for each specific blocker and summarized bar graphs are shown (FIG. 5A, B). Next, the activity of the nifedipine-sensitive VGCCs was studied using the whole-cell patch clamp configuration (FIG. 2C). Islet cells treated with serum from ALS patients displayed larger $Ca^{2+}$ currents than islet cells treated with control serum. Currents were elicited by 300 ms voltage steps between −60 and 40 mV from a holding potential of −70 mV (FIG. 2C). FIG. 2C shows the current-voltage (I-V) relationships of nifedipine-sensitive VGCCs in islet cells which were incubated with sera from two ALS patients and one control patient. Incubation with ALS serum dramatically increased whole cell $Ca^{2+}$ currents, as manifested by representative whole-cell $Ca^{2+}$ current traces obtained from a control cell and a cell treated with ALS serum (FIG. 2C). Compiled data show that ALS serum significantly elevated whole cell $Ca^{2+}$ current density measured at the depolarization −20 mV compared to control serum (FIG. 2C).

Figure 6:
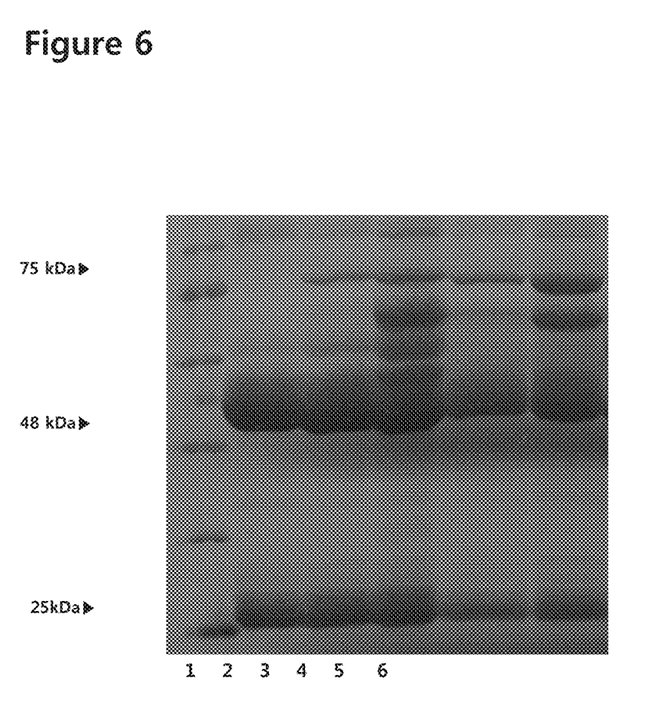
FIG. 6. IgGs were purified from different sera, identified by SDS-PAGE (6-16%) and stained by Coomassie brilliant blue. Lane 1: Molecular weight markers (molecular weight range 10-245 kDa, Solgent), Lane 2: Human IgG from Sigma, Lane 3: CTL-7 IgG, Lane 4: CTL-7 IgG, Lane 5: ALS-374 IgG and Lane 6: ALS-374 IgG. The preparations shown in lanes 4 and 6 contained both IgG and non-IgG components.
Figure 7:
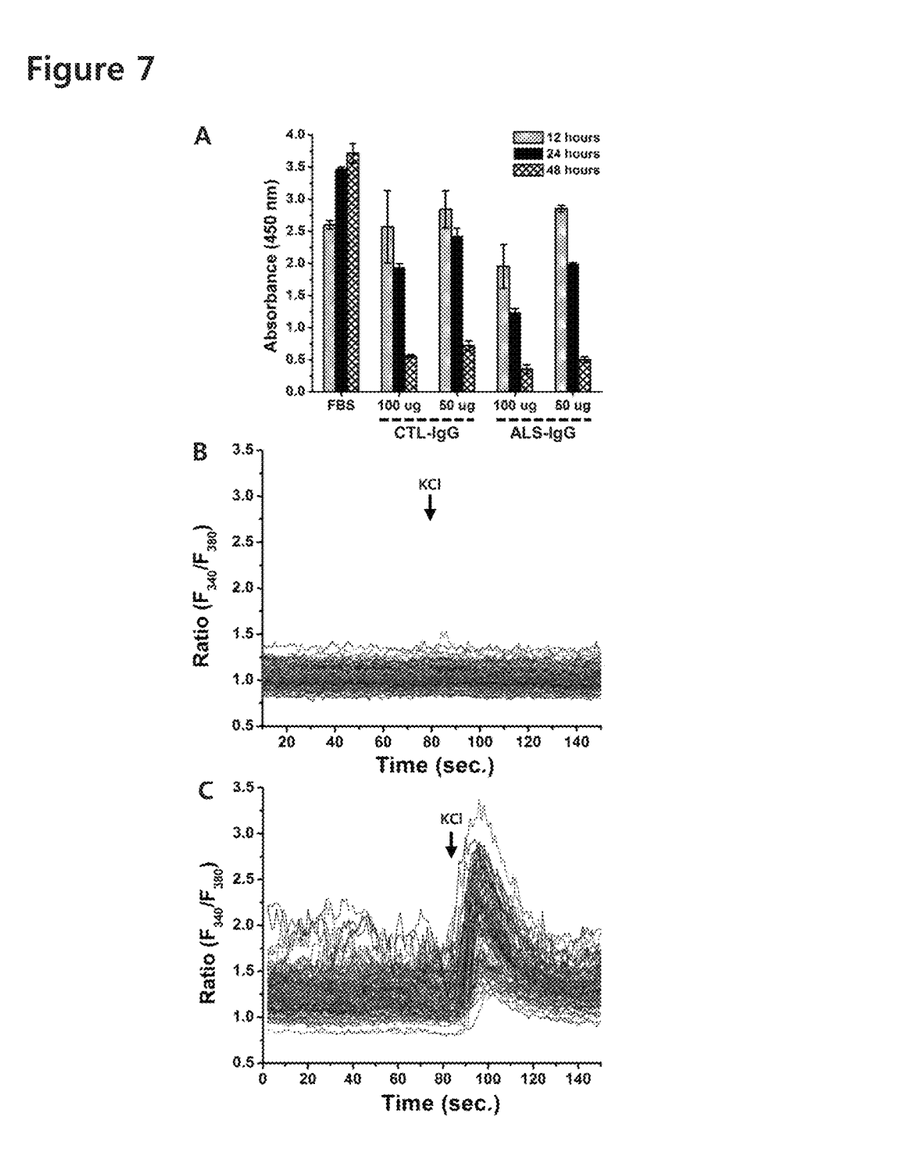

To clarify the extent to which the effect of ALS serum was specific to the insulin-secreting pancreatic beta cell or had a more general effect on islet cells, we tested a glucagon-secreting mouse pancreatic alpha-cell line, αTC1-6 cells. Also in these cells, ALS serum induced an increase in $[Ca^{2+}]_i$ subsequent to $K^+$-induced depolarization that was more prominent than the increase obtained when the cells were exposed to control serum (FIG. 2E, F). In αTC1-6 cells nifedipine-sensitive VGCCs were the most abundant $Ca^{2+}$ channels responsible for mediating the increase in $[Ca^{2+}]_i$ (Supplementary FIG. 2C and FIG. 6B, C). However, since αTC1-6 cells also have a considerable number of ω-agatoxin TK (AgTx)-sensitive $Ca^{2+}$ channels, i.e. P/Q-type VGCCs, these could also be involved in mediating the effect on $[Ca^{2+}]_i$. Furthermore, cytotoxicity is prevalent in αTC1-6 cells treated with serum from of ALS patients compared to serum from control patients (FIG. 2G and FIG. 7A). Hence, serum taken from ALS patients with T2DM affects not only insulin-secreting beta cells but also glucagon-secreting alpha cells, demonstrating a more broad interference with hormone secretion in the endocrine pancreas. Since both insulin and glucagon have vital roles in glucose homeostasis, these disturbances are likely to play a major role in diabetes pathogenesis.

Figure 3:
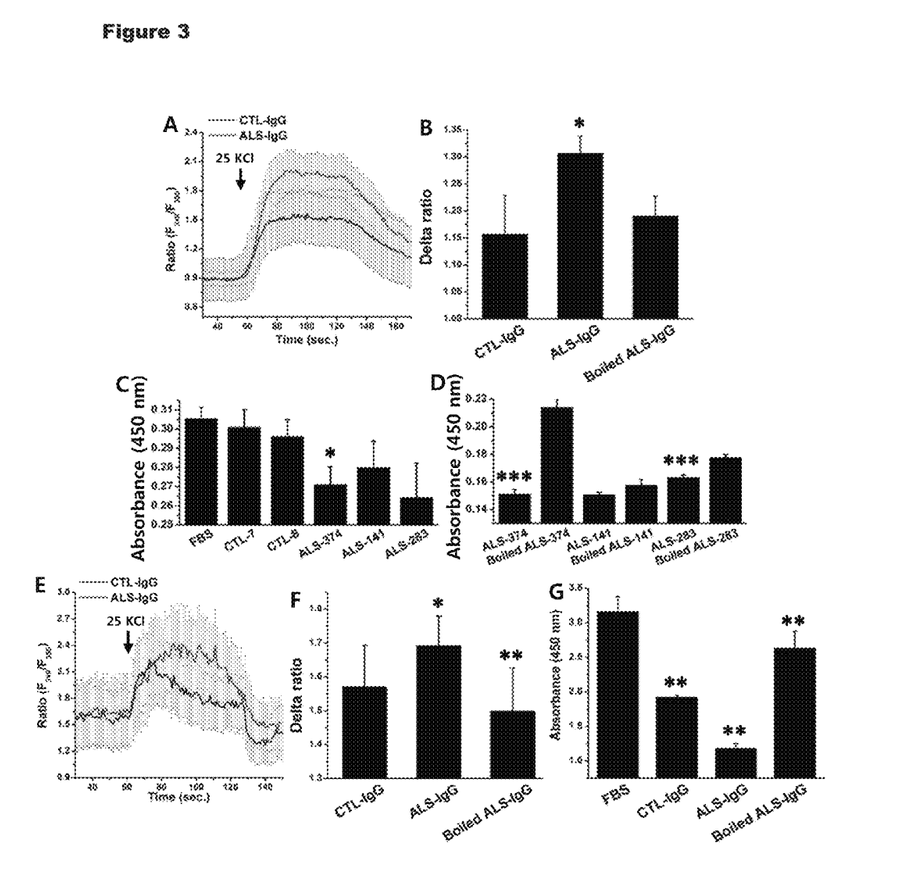

Looking for a circulating component mediating the effect on islet cell $[Ca^{2+}]_i$ handling in ALS serum, we turned our interest to IgG. This immunoglobulin was purified from ALS serum and control serum (FIG. 6, lanes 3 and 5). Human IgG from Sigma was used as positive control. All preparations of serum-IgG and IgG from Sigma showed two main bands in electrophoresis, one for the 55 kDa heavy chain and one for the 26 kDa light chain. Each purified serum-IgG sample was lyophilized for enrichment and used to treat dissociated pancreatic islet cells and αTC1-6 cells at a concentration of 100 μg IgG/ml. In the presence of ALS-IgG, compared to control IgG, there was a more pronounced transient $[Ca^{2+}]_i$ increase subsequent to high $K^+$ exposure in both dissociated islet cells (FIG. 3A, B) and αTC1-6 cells (FIG. 3E, F). The effect on $[Ca^{2-}]_i$ was attenuated when ALS-IgG was boiled for 30 minutes at 96° C. Moreover, we also checked cellular cytotoxicity of ALS-IgG (FIG. 3C, D, G). Cells exposed to ALS-IgG exhibited less survival compared to cells exposed to control IgG (FIG. 3C, D, G).

Our findings thus indicate that the reported glucose homeostasis abnormalities in ALS patients (10, 29, 30) can be explained by a functional deficiency in islet cell $[Ca^{2+}]_i$ handling, due to an IgG-mediated activation of VCCS, and thereby islet cell death.

Methods

Islet Isolation and Islet Cell Culture

Pancreatic islets were isolated by standard collagenase digestion and subsequently handpicked under a stereomicroscope in RPMI 1640 culture medium. Single cells were obtained by shaking the islets in $Ca^{2+}$-free medium with ACCUTASE® (Gibco) and seeded onto glass coverslips. Islets and single cells were cultured in RPMI 1640 medium supplemented with 10% fetal bovine serum, 2 mM L-glutamine, and 100 U/100 μg/ml penicillin/streptomycin and maintained at 37° C. in humidified atmosphere of 5% $CO_2$ in air.

Enrollment of Patients

Twelve patients with sporadic ALS and T2DM and patients with T2DM without ALS were randomly selected. Ethical approval to use serum from patients was obtained from Hanyang University Hospital in Seoul, Korea (HYUH 2006-04-001-004). Blood samples were collected after obtaining written informed consent. Actual patients had no known family history of neuromuscular disease or wasting. All subjects diagnosed with T2DM were well-controlled with hypoglycemic agents.

Preparation of Serum and IgG Purification

Sera from ALS patients with T2DM and control subjects with T2DM without ALS were collected, identically sterile-processed, and stored at −20° C. until used. The sera were heat-inactivated by incubation at 56° C. for 30 min. Cells were incubated overnight in RPMI 1640 culture medium supplemented with 10% of the actual serum. Serum IgG was purified using specific gel-based spin column purification (IgG purification resin; Pierce/Thermo Fisher Scientific). The IgG purification kit was based on a resin containing a proprietary ligand that only allows IgG to pass through. The column support was used to remove non-antibody serum proteins and isolate serum IgG. Briefly, 500 μl diluted serum was added to the mini-spin columns prepared according to the manufacturer's instructions, and IgG was eluted by centrifugation at 3000G. Eluted fractions were concentrated by lyophilizer and tested by sodium dodecyl sulfate polyacrylamide gel electrophoresis (SDS-PAGE) before used on cells.

Measurements of $[Ca^{2+}]_i$

Islets and single cells attached to coverslips were pre-treated with the different patient sera and then loaded with 2 μM fura-2/AM for 30 min at 37° C. in HEPES buffered solution containing (in mM) 125 NaCl 5.9 KCl 2.56 $CaCl_2$, 1.2 $MgCl_2$, 25 HEPES, and 3 glucose (pH 7.4). A glucose concentration of 11 mM was used for islet stimulation. After loading, islets and cells on the glass coverslips were transferred to an open perifusion chamber maintained at 37° C. and $[Ca^{2+}]_i$ measured as the 340/380 nm ratio. The light source was equipped with a xenon arc lamp and an integrated shutter (Lambda DG-4, Sutter instrument company), and coupled to the microscope (Olympus ix 71) via a liquid light guide. The 16-bit grayscale images with a binning of 1×1 were captured every 1 s (exposure time ranged from 100 to 300 ms) with a cooled EM-CCD camera (ImagEM X2, Hamamatsu). The camera and shutter were controlled by METAFLUOR® (Molecular Devices) software, which was also used for analysis. Cells with bright $[Ca^{2+}]_i$ signal defined the regions of interest (ROIs). ROI signals were calculated by subtracting background noise signal.

Electrophysiological Recordings

Mouse islet cells following different treatments were subjected to conventional whole-cell patch-clamp analysis with an EPC-10 patch clamp amplifier (HEKA Elektronik, Lambrecht/Pfalz, Germany). Cells were bathed in the following external solution (in mM): 138 NaCl, 10 TEACl, 10 $CaCl_2$, 5.6 KCl, 1.2 $MgCl_2$, 5 HEPES, and 3 glucose (pH 7.4). The pipette solution contained (in mM) 150 N-methy-D-glucamine, 125 HCl, 10 EGTA, 1.2 $MgCl_2$, 3 Mg-ATP, and 5 HEPES (pH 7.15). Borosilicate glass electrodes (1.2 mm outside diameter, Warner Instrument) were pulled with a vertical pipette puller (PC-10, Narishige), and had tip resistances ranging between 2 and 3 MΩ when filled with pipette solution. All recordings were performed at room temperature. The amplitude of whole-cell $Ca^{2+}$ currents was normalized by cell capacitance. Acquisition and analysis of data were done using the software program PATCHMASTER® (HEKA Elektronik). Most of chemicals were ordered from Sigma-Aldrich and nifedipine and ω-agatoxin TK were from Tocris.

Glucose Tolerance Tests and Insulin Release

For the glucose tolerance tests, mice were injected intraperitoneally with D-glucose solution (2 g/kg body weight) following an overnight fast. Blood was collected from the tail vein at 15, 30, 60, and 120 min after the glucose injection and then blood glucose levels were determined using a glucometer (ACCU-CHECK ACTIVE®, Roche Diagnostics). Measurements of glucose-induced insulin secretion were performed with isolated islets subjected to overnight culture. Ten islets were pooled in batches and incubated at 37° C. for 30 min in a HEPES buffered solution (pH 7.4) containing (in mM) 125 NaCl, 5.9 KCl, 1.2 $MgCl_2$, 2.56 $CaCl_2$, and 3 or 11 glucose supplemented with BSA at a concentration of 1 mg/ml. Supernatants were carefully aspirated and static insulin secretion from the islets was assayed using the mouse insulin ELISA kit (ALPCO).

WST-1 Assay

Cell viability was assessed under the different experimental conditions using the PreMix Water-Soluble Tetrazolium Salt (WST-1) Cell Proliferation Assay System (Takara Bio Inc.). Cells were seeded in a 96-well microplate and cultivated for 12 and 24 hours in experiments with sera and purified IgGs, respectively. Subsequently, the culture medium was replaced with a 10:1 solution of the fresh culture medium and WST-1 reagent. The microplate was incubated for 4 hours at 37° C. and then metabolically active viable cells were quantified by measuring absorbance at 450 nm in a microplate reader.

REFERENCES

1. Brooks B R. Natural history of ALS: symptoms, strength, pulmonary function, and disability. *Neurology* 1996; 47(4 Suppl 2):S71-81.
2. Smith R G, Alexianu M E, Crawford G, Nyormoi O, Stefani E, Appel S H. Cytotoxicity of immunoglobulins from amyotrophic lateral sclerosis patients on a hybrid motoneuron cell line. *Proc Natl Acad Sci USA.* 1994; 91(8):3393-3397.
3. Tran L T, Gentil B J, Sullivan K E, Durham H D. The voltage-gated calcium channel blocker lomerizine is neuroprotective in motor neurons expressing mutant SOD1, but not TDP-43. *J Neurochem.* 2014; 130(3):455-466.
4. Pullen A H, Demestre M, Howard R S, Orrell R W. Passive transfer of purified IgG from patients with amyotrophic lateral sclerosis to mice results in degeneration of motor neurons accompanied by $Ca^{2+}$ enhancement. *Acta Neuropathol.* 2004; 107(1):35-46.
5. Billups B, Forsythe I D. Presynaptic mitochondrial calcium sequestration influences transmission at mammalian central synapses. *J Neurosci.* 2002; 22(14):5840-5847.
6. Shi P, Gal J, Kwinter D M, Liu X, Zhu H. Mitochondrial dysfunction in amyotrophic lateral sclerosis. *Biochim Biophys Acta.* 2010; 1802(1):45-51.
7. Barber S C, Shaw P J. Oxidative stress in ALS: key role in motor neuron injury and therapeutic target. *Free Radic Biol Med.* 2010; 48(5):629-641.
8. Craft S, Watson G S. Insulin and neurodegenerative disease: shared and specific mechanisms. *Lancet Neurol.* 2004; 3 (3): 169-178.
9. Park S A. A common pathogenic mechanism linking type-2 diabetes and Alzheimer's disease: evidence from animal models. *J Clin Neurol.* 2011; 7(1):10-18.
10. Pradat P F, et al. Impaired glucose tolerance in patients with amyotrophic lateral sclerosis. *Amyotroph Lateral Scler.* 2010; 11(1-2): 166-171.
11. Rosen D R, et al. Mutations in Cu/Zn superoxide dismutase gene are associated with familial amyotrophic lateral sclerosis. *Nature.* 1993; 362(6415): 59-62.
12. Renton A E, Chio A, Traynor B J. State of play in amyotrophic lateral sclerosis genetics. *Nat Neurosci.* 2014; 17(1): 17-23.
13. Robberecht W, Philips T. The changing scene of amyotrophic lateral sclerosis. *Nat Rev Neurosci.* 2013; 14(4): 248-264.
14. Appel S H, Zhao W, Beers D R, Henkel J S. The microglial-motoneuron dialogue in ALS. *Acta Myol.* 2011; 30(1):4-8.
15. Berggren P O, et al. Removal of $Ca^{2-}$ channel $\beta_3$ subunit enhances $Ca^{2+}$ oscillation frequency and insulin exocytosis. *Cell.* 2004; 119(2):273-284.
16. Fridlyand L E, Tamarina N, Philipson L H. Bursting and calcium oscillations in pancreatic beta-cells: specific pacemakers for specific mechanisms. *Am J Physiol Endocrinol Metab.* 2010; 299(4):E517-532.
17. Rorsman P, Braun M, Zhang Q. Regulation of calcium in pancreatic α- and β-cells in health and disease. *Cell Calcium.* 2012; 51(3-4):300-308.
18. Yang S N, Berggren P O. The role of voltage-gated calcium channels in pancreatic β-cell physiology and pathophysiology. *Endocr. Rev.* 2006; 27(6):621-676.
19. Yang S N, Shi Y, Yang G, Li Y, Yu J, Berggren P O. Ionic mechanisms in pancreatic beta cell signaling. *Cell Mol Life Sci.* 2014; 71(21):4149-4177.
20. Smith R G, et al. Serum antibodies to L-type calcium channels in patients with amyotrophic lateral sclerosis. *N Engl J Med.* 1992; 327(24):1721-1728.
21. Kimura F, et al. Amyotrophic lateral sclerosis patient antibodies label $Ca^{2+}$ channel alpha 1 subunit. *Ann Neurol.* 1994; 35(2): 164-171.
22. Fratantoni S A, Weisz G, Pardal A M, Reisin R C, Uchitel O D. Amyotrophic lateral sclerosis IgG-treated neuromuscular junctions develop sensitivity to L-type calcium channel blocker. *Muscle Nerve.* 2000; 23(4):543-550.
23. Gonzalez L E, et al. Amyotrophic lateral sclerosis-immunoglobulins selectively interact with neuromuscular junctions expressing P/Q-type calcium channels. *J Neurochem.* 2011; 119(4): 826-838.
24. Milosevic M, et al. Immunoglobulins G from patients with sporadic amyotrophic lateral sclerosis affects cytosolic $Ca^{2+}$ homeostasis in cultured rat astrocytes. *Cell Calcium.* 2013; 54(1):17-25.
25. Llinas R, et al. IgG from amyotrophic lateral sclerosis patients increases current through P-type calcium channels in mammalian cerebellar Purkinje cells and in isolated channel protein in lipid bilayer. *Proc Natl Acad Sci USA.* 1993; 90(24):11743-11747.
26. Mosier D R, et al. Amyotrophic lateral sclerosis immunoglobulins increase $Ca^{2+}$ currents in a motoneuron cell line. *Ann Neurol.* 1995; 37(1):102-109.
27. Losavio A, Muchnik S. Spontaneous acetylcholine release in mammalian neuromuscular junctions. *The American journal of physiology.* 1997; 273(6 Pt 1):C1835-1841.
28. Muchnik S, Losavio A, De Lorenzo S. Effect of amyotrophic lateral sclerosis serum on calcium channels related to spontaneous acetylcholine release. *Clin Neurophysiol.* 2002; 113(7):1066-1071.
29. Dupuis L, Oudart H, Rene F, Gonzalez de Aguilar J L, Loeffler J P. Evidence for defective energy homeostasis in amyotrophic lateral sclerosis: benefit of a high-energy diet in a transgenic mouse model. *Proc Natl Acad Sci USA.* 2004; 101(30):11159-11164.
30. Jawaid A, et al. ALS disease onset may occur later in patients with pre-morbid diabetes mellitus. *Eur J Neurol.* 2010; 17(5):733-739.

I claim:

1. A method for treating and/or for limiting development of type 2 diabetes in a subject with amyotrophic lateral sclerosis (ALS), comprising inhibiting IgG-mediated activation of voltage-gated calcium channels (VGCCs) in cells of the subject, wherein the inhibiting comprises:
   removing IgG from blood of the subject to produce IgG-depleted blood, and wherein the method further comprises administering the IgG-depleted blood to the subject, thus treating and/or limiting development of type 2 diabetes in the subject.

2. The method of claim 1, wherein removing serum IgG from the subject comprises contacting blood obtained from the subject with an IgG adsorbent to promote IgG adsorption onto the adsorbent.

3. The method of claim 2, wherein the IgG adsorbent comprises anti-human IgG antibodies.

4. The method of claim 1, wherein the subject has type 2 diabetes and the method serves to treat type 2 diabetes.

5. The method of claim 1, wherein the subject does not yet have type 2 diabetes and the method serves to limit development of type 2 diabetes.

6. The method of claim 5, wherein limiting development of type 2 diabetes comprises slowing progression of hyperglycemia and/or insulin resistance in the subject.

7. The method of claim 2, wherein the subject has type 2 diabetes and the method serves to treat type 2 diabetes.

8. The method of claim 2, wherein the subject does not yet have type 2 diabetes and the method serves to limit development of type 2 diabetes.

9. The method of claim 8, wherein limiting development of type 2 diabetes comprises slowing progression of hyperglycemia and/or insulin resistance in the subject.

10. The method of claim 3, wherein the subject has type 2 diabetes and the method serves to treat type 2 diabetes.

11. The method of claim 3, wherein the subject does not yet have type 2 diabetes and the method serves to limit development of type 2 diabetes.

12. The method of claim 8, wherein limiting development of type 2 diabetes comprises slowing progression of hyperglycemia and/or insulin resistance in the subject.

* * * * *